United States Patent [19]

Soderman

[11] Plant 4,697

[45] Apr. 21, 1981

[54] CHRYSANTHEMUM PLANT

[75] Inventor: Phillip A. Soderman, Carpinteria, Calif.

[73] Assignee: Sandyland Nursery Company, Inc., Carpinteria, Calif.

[21] Appl. No.: 102,967

[22] Filed: Dec. 12, 1979

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant with flat daisy capitulum which is a sport of the cultivar Gem, being distinguished from the parent cultivar by its light lavender pink (commercially acceptable as white) ray floret color.

2 Drawing Figures

1

The present invention comprises a new and distinct cultivar of *Chrysanthemum morifolium,* Ramat., hereinafter referred to by the cultivar name of White Gem.

White Gem is a spontaneous mutation of the cultivar Gem, disclosed in U.S. Plant Pat. No. 3,740, and was selected to expand the color range of the parental variety.

White Gem was discovered and selected by Phillip A. Soderman on Mar. 22, 1977 as one plant within a flowering block of Gem in Carpinteria, Calif. The first act of asexual reproduction of White Gem was accomplished on June 8, 1977 when vegetative cuttings were taken from the initial selection in Carpinteria, Calif. by Phillip A. Soderman.

Continued asexual reproduction by vegetative cuttings for evaluative flowering programs in conjunction with horticultural examination of selected units initiated June 29, 1978 has demonstrated that the combination of characteristics as herein disclosed for White Gem are firmly fixed and are retained through successive generations of asexual reproduction.

White Gem has not been observed under all possible environmental conditions. The phenotype may vary significantly with variations in environment such as temperature, light intensity and daylength. The following observations, measurements and comparisons describe plants grown in Carpinteria, Calif. and Salinas, Calif. under environmental conditions which approximate those generally used in commercial practice.

The following traits have been repeatedly observed and are determined to be basic characteristics of White Gem which in combination distinguish this chrysanthemum as a new and distinct cultivar:

(1) daisy capitulum type, (2) flat capitulum form, (3) light lavender pink ray floret color, oxidizing rapidly to white (commercially acceptable as white), (4) diameter across face of inflorescence ranging from 70 to 88 mm. at maturity, (5) uniform seven week photoperiodic flowering response, (6) tall plant height (requiring 1-2 long day weeks prior to pinch and short days, and 2-3 applications 2500 ppm B-9 SP 7 to 21 days after pinch to attain a flowered plant height of 30 to 35 cm. when grown as a pinched spray pot plant for May through October flowerings in Salinas, Calif.), and (7) upright branching pattern.

2

The accompanying color photographic drawing shows typical inflorescense and foliage characteristics of White Gem, with the colors being as nearly true as possible with photographs of this type. Sheet 1 is a color photograph of the inflorescence of White Gem grown in a cool environment (approximately 56°-58° F. night temperature) without color-diluting growth retardants. Sheet 2 is a color photograph of a four plant, six inch pot of White Gem grown in a warm environment (approximately 60° F. to 62° F. night temperatures) and given 3 applications 2500 ppm B-9 SP for height control.

Of the many commercial cultivars known to the present inventors, the most similar in comparison to White Gem is Gem. Reference is made to attached Chart A which compares certain characteristics of White Gem with the same characteristics of Gem. As noted in Chart A, White Gem has different ray floret color than Gem, with other characteristics of White Gem being similar to those same characteristics of Gem.

In the following description, color references are made to A Limit Color Cascade, published by the Munsell Company, 1972 edition. The color values were determined between 9:00 and 9:30 a.m. on May 10, 1979 under 75 foot-candle light intensity at Salinas, Calif.

Classification:

*Botanical.*—*Chrysanthemum morifolium,* Ramat., cv White Gem.

*Commercial.*—Pinched spray pot.

I. Inflorescence:

A. *Capitulum.*—Form: Flat. Type: Daisy. Permanence: 14 to 18 days. Diameter across face: 70 to 88 mm.

B. *Corolla of ray florets.*—Color (general tonality): White. Color (abaxial): Approximately 45-2 oxidizing rapidly to white. Color (adaxial): 45-1 oxidizing to white.

C. *Corolla of disc florets.*—Color (mature): 27-6. Color (immature): 22-11.

D. *Reproductive organs.*—Androecium: Present disc florets only; moderate pollen, most abundant under low light conditions. Gynoecium: Present both ray and disc florets.

II. Plant:

A. *General appearance.*—Branching pattern: Upright. Height: Tall (pot mum culture).

B. *Foliage.*—Color (abaxial): Approximately 21-14. Color (adaxial): Approximately 21-14 overlaid with white.

CHART A

COMPARISON OF WHITE GEM AND GEM

| Cultivar | Ray Floret Color | Diameter Across Face Of Capitulum | Plant Height | Branching Pattern | Flowering Response Period | Capitulum Form & Type |
|---|---|---|---|---|---|---|
| White Gem | Light Lavender pink (commercial white) | 70 to 88 mm. | Tall | Upright | 7 week | Flat Daisy |

CHART A-continued

COMPARISON OF WHITE GEM AND GEM

| Cultivar | Ray Floret Color | Diameter Across Face Of Capitulum | Plant Height | Branching Pattern | Flowering Response Period | Capitulum Form & Type |
|---|---|---|---|---|---|---|
| Gem | Lavender Pink | 70 to 88 mm. | Tall | Up right | 7 week | Flat Daisy |

COMPARISONS MADE OF PINCHED SPRAY PLANTS GROWN IN CARPINTERIA, CALIFORNIA AND SALINAS, CALIFORNIA.

I claim:

1. A new and distinct cultivar of *Chrysanthemum morifolium,* Ramat., known by the cultivar name White Gem, as described and illustrated, and particularly characterized as to uniqueness by the combined characteristics of daisy capitulum type; flat capitulum form; light lavender pink ray floret color (commercially acceptable white); diameter across face of capitulum ranging from 70 to 88 mm. at maturity; uniform seven week flowering response to photoperiodic short day control; tall plant height, and upright branching pattern.

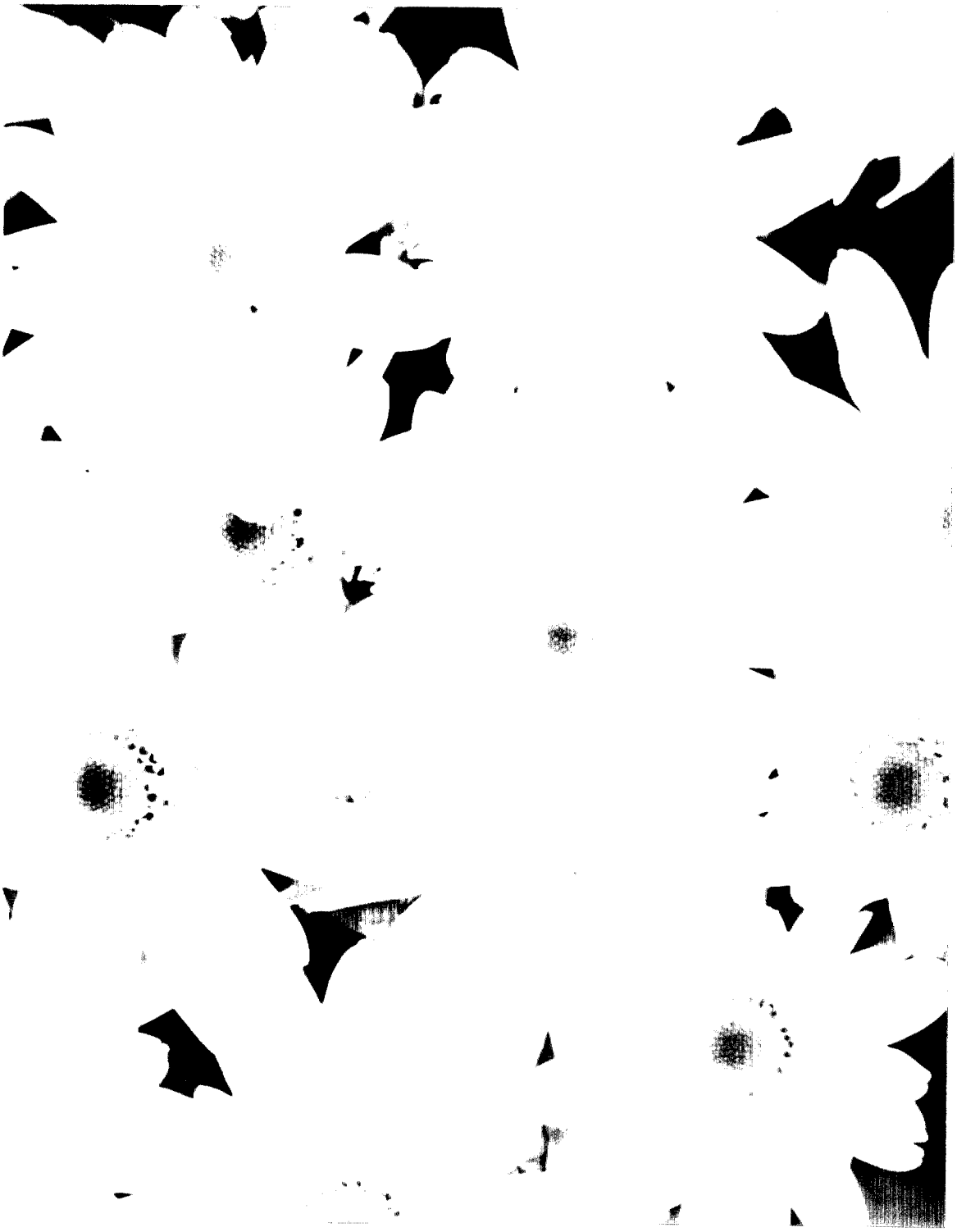

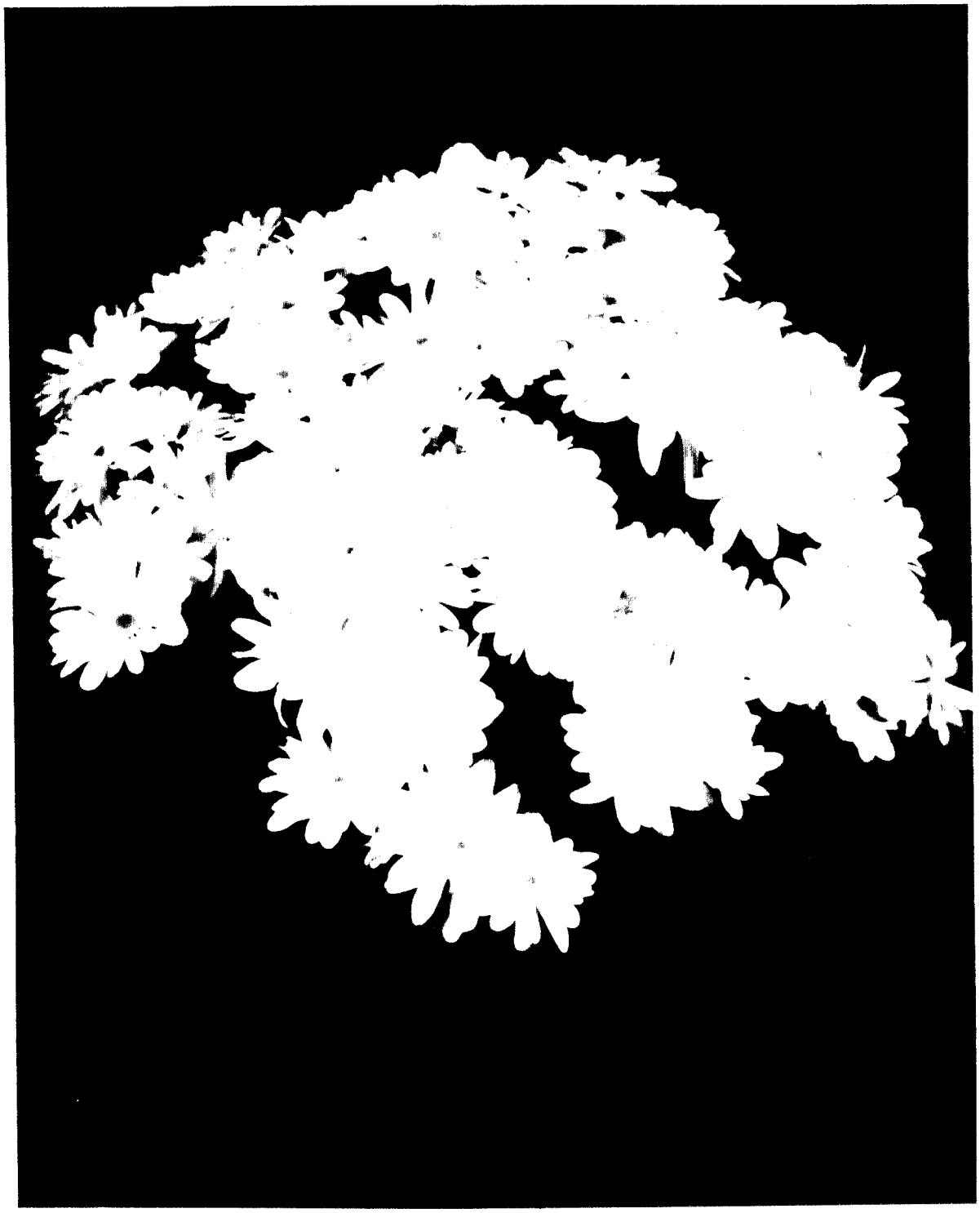

* * * * *